United States Patent
Hauri et al.

(10) Patent No.: US 6,770,098 B1
(45) Date of Patent: Aug. 3, 2004

(54) KNEE-JOINT ENDOPROSTHESIS

(75) Inventors: Thomas Hauri, Staffelbach (CH); Bernhard Hauri, Staffelbach (CH); Hans Schmotzer, Zürich (CH); Werner Berner, Erlinsbach (CH)

(73) Assignee: Plus Endoprothetik AG (CH)

( * ) Notice: Subject to any disclaimer, the term of this patent is extended or adjusted under 35 U.S.C. 154(b) by 0 days.

(21) Appl. No.: 10/111,117

(22) PCT Filed: Oct. 17, 2000

(86) PCT No.: PCT/EP00/10235
§ 371 (c)(1),
(2), (4) Date: Sep. 4, 2002

(87) PCT Pub. No.: WO01/28462
PCT Pub. Date: Apr. 26, 2001

(30) Foreign Application Priority Data

Oct. 18, 1999 (DE) .......................... 199 50 112

(51) Int. Cl.[7] ................................................. A61F 2/38
(52) U.S. Cl. .................................................. 623/20.26
(58) Field of Search .................... 623/18.11, 20.24, 623/20.26, 20.32, 20.33

(56) References Cited

U.S. PATENT DOCUMENTS

| | | | |
|---|---|---|---|
| 3,824,630 A | | 7/1974 | Johnston ............................. 1/1 |
| 6,139,580 A | * | 10/2000 | Wurzinger et al. ...... 623/20.26 |
| 6,210,444 B1 | * | 4/2001 | Webster et al. ........... 623/20.33 |
| 6,217,618 B1 | * | 4/2001 | Hileman ................... 623/20.33 |
| 6,238,434 B1 | * | 5/2001 | Pappas ..................... 623/20.29 |
| 6,319,283 B1 | * | 11/2001 | Insall et al. ............... 623/20.33 |
| 6,361,564 B1 | * | 3/2002 | Marceaux et al. ........ 623/20.29 |
| 6,491,726 B2 | * | 12/2002 | Pappas ..................... 623/20.29 |
| 6,558,427 B2 | * | 5/2003 | Leclercq et al. .......... 623/20.33 |

FOREIGN PATENT DOCUMENTS

| | | |
|---|---|---|
| EP | 0 529 408 B1 | 3/1993 |
| EP | 0 519 873 B1 | 12/1996 |

* cited by examiner

Primary Examiner—Pedro Philogene
Assistant Examiner—David A Bonderer
(74) Attorney, Agent, or Firm—Knobbe, Martens, Olson & Bear LLP

(57) ABSTRACT

A knee-joint prosthesis with a tibial part having a flat tibial bearing surface, with a bearing body that can be shifted thereon in the anterior-posterior direction and includes two concave bearing shells within which a femoral joint part can be movably seated, and with a rotational guide that permits rotation of the bearing body on the tibial bearing surface about an axis of rotation perpendicular to said surface. The rotation guide includes a steering rod that is seated at the bearing body so as to be pivotable relative thereto and at the tibial part is guided in the medial/lateral direction and/or rotationally guided.

39 Claims, 5 Drawing Sheets

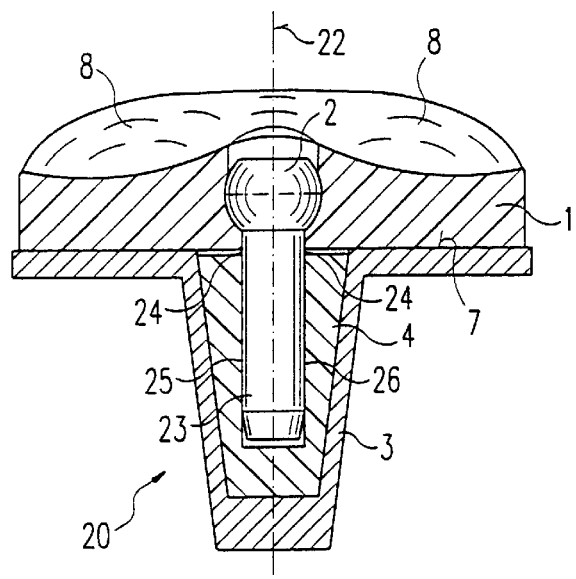
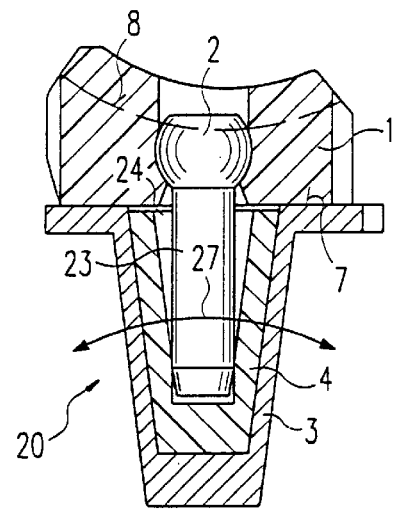
Fig. 2
Fig. 1
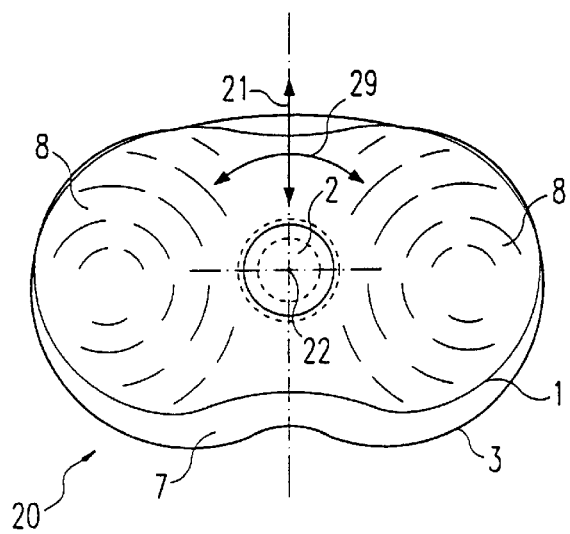
Fig. 3

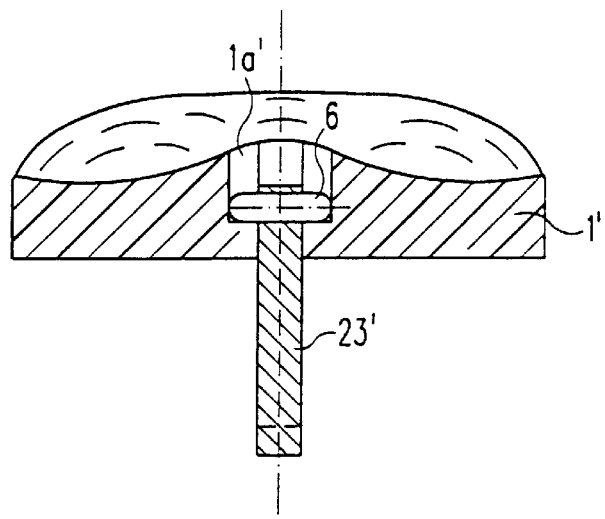
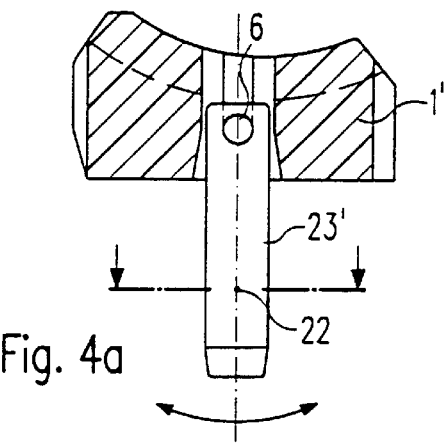
Fig. 5
Fig. 4a

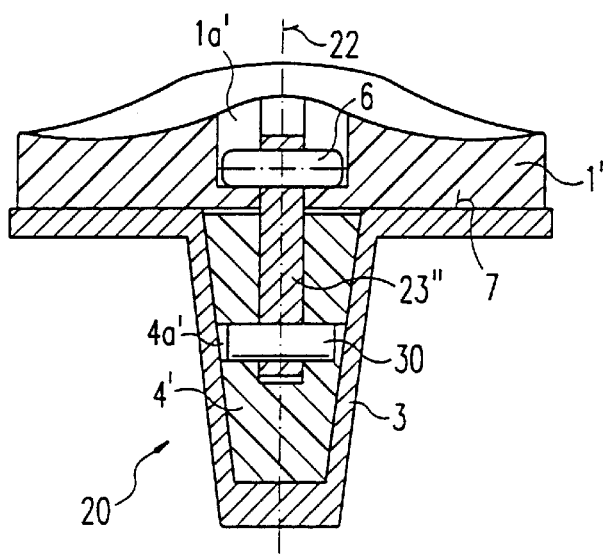
Fig. 6 (B-B)

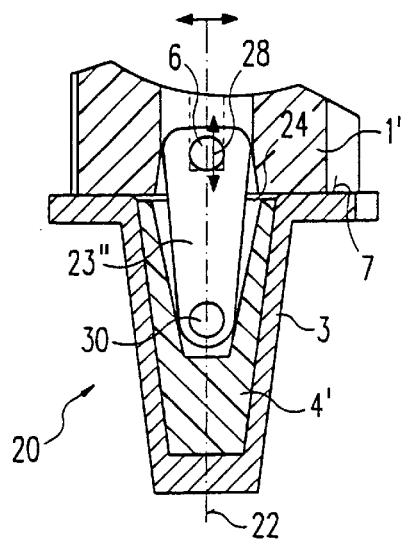
Fig. 7 (A-A)
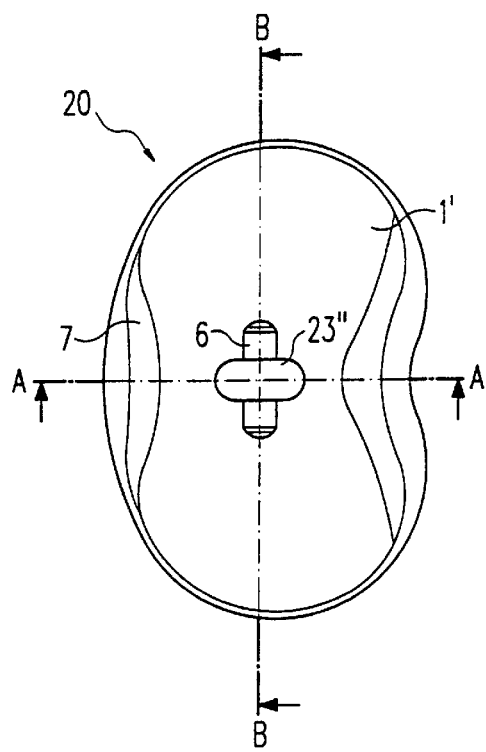
Fig. 8
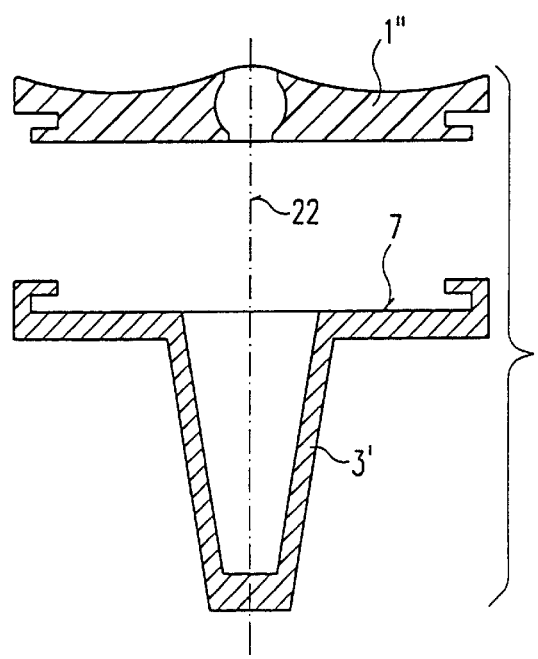
Fig. 9

KNEE-JOINT ENDOPROSTHESIS

RELATED APPLICATIONS

This application claims the benefit of the German patent application No. 199 50 112.2 filed Oct. 18, 1999, the European patent application No. 00 110 627.7 filed May 18, 2000, and the international application PCT/EP00/10235 filed Oct. 17, 2000.

BACKGROUND OF THE INVENTION

The invention relates to a knee-joint endoprosthesis with a tibial part having a flat tibial bearing surface, a bearing body that can be displaced thereon in the anterior-posterior direction and comprises two concave bearing shells within which a femoral joint part can be movably supported, and a rotational guide means that permits rotation of the bearing body on the tibial bearing surface about an axis perpendicular to the latter.

DESCRIPTION OF THE RELATED ART

A knee-joint endoprosthesis of this kind is known, for example, from the patents EP 0 529 408 B1 or EP 0 519 873 B1.

Both of these known constructions represent knee-joint endoprostheses that comprise not only joint-surface congruence and the translational mobility of a so-called meniscus knee, but also preserve these properties even during rotational movements and to a great extent ensure protection against luxation of the bearing body and enable movements to occur in a nearly normal, physiological manner.

The construction according to EP 0 519 873 B1 is characterized by the fact that the translational movement of the bearing body is not limited by stopping devices.

However, it has been found that soft tissues can then very easily become irritated and the cruciate ligaments can be overloaded.

Furthermore, it should be possible for the surgeon to wait until the closing phase of an operation to decide whether the knee implant employed should permit both translation and rotation or only rotation of the bearing body. With the known constructions, the surgeon does not have this choice.

Finally, the surgeon should have the opportunity during the closing phase of the operation to determine the maximal translational movement of the bearing body in the posterior-anterior direction.

Accordingly, it is the objective of the present invention to create a knee-joint endoprosthesis of the kind described above that avoids the above-mentioned disadvantages of the known constructions, provides maximal degrees of freedom for guidance suitable to the anatomy, and does not irritate soft parts or overload the cruciate ligaments. Furthermore, this construction should largely avoid excessive complexity in the sliding bearing between bearing body and tibial bearing surface, and should operate without bending moments.

SUMMARY OF THE INVENTION

This objective is achieved by the characterizing features given in claim 1. That is, the knee-joint endoprosthesis in accordance with the invention is characterized in that the rotational guide means for the bearing body comprises a steering rod that is mounted so as to be pivotable relative to the bearing body and at the tibial part is guided in a medial/lateral direction and/or rotationally.

Structural details of the knee-joint endoprosthesis in accordance with the invention are described in the subordinate claims.

In one advantageous embodiment, at the tibial part the steering rod is guided medially and laterally within an aperture in the form of slot that extends in the anterior-posterior direction. At the bearing body, in contrast, it is either mounted so as to be rotatable and pivotable relative thereto or it is so mounted that together with the aperture in the tibial part (i.e., the component incorporating the aperture) it can be rotated about an axis perpendicular to the tibial bearing surface.

Another preferred embodiment is characterized by the fact that the slot at the level of the tibial bearing surface delimits a recess in the form of a pocket hole, which is situated within a distally extending tibial housing and expands in a trapezoidal form, at least in its upper region, from distal to proximal in the anterior-posterior direction. In another preferred development the recess is also trapezoidally expanded towards its floor, so that the steering rod can be pivoted with no bending moment about an axis of rotation spaced apart from its lower end (situated at the level of the narrowest part of the recess).

Medially and laterally the pocket hole is delimited by walls that extend parallel to one another and approximately perpendicular to the tibial bearing surface, which are spaced apart from one another by a distance slightly greater than the diameter of the steering rod, or section thereof, that is contained within the pocket hole. The rod or rod section should be guided so that it can slide with medial and lateral clearance.

The pivot bearing of the steering rod in accordance with the invention in the anterior-posterior direction is achieved in a variant by providing the proximal end of the rod with a spherical head that inserts into a complementarily formed pivot-bearing recess in the bearing body; in particular, the head can be locked therein. Alternatively, at the proximal end of the steering rod there can be provided a pivotal axis that extends approximately parallel to the tibial bearing surface in the medial/lateral direction, which likewise engages a complementary pivot-bearing recess in the bearing housing.

The sliding bearing of the steering rod at the tibial part is advantageously implemented within a bearing sleeve made of plastic, in particular polyethylene, and positioned at the tibial part so as to be secured against rotation, in particular is disposed within a tibial housing that extends distally. This arrangement ensures that after the operation the slideway of the steering rod remains exactly in the posterior-anterior direction.

In a special embodiment the slot-like recess is curved so as to be concave towards the medial side, i.e. convex towards the lateral side. In particular, it has the shape of an arc of a circle, with a center of curvature situated medially, in particular within the contour of the bearing body. The steering rod or section thereof (steering shaft) that interacts with this recess preferably has a cross-sectional shape that is either circular or comprises two curved wall sections that match the curved shape of the recess.

Otherwise, the steering rod or the section thereof that passes is contained in the recess is shaped to suit a recess with flat wall sections; that is, it is either circular in cross section or its cross section comprises two lateral semicircles connected by straight lines.

In an alternative embodiment the steering rod is pivotably seated by its distal end at the tibial part, such that this distal and/or the proximal pivot bearing at the bearing body permits a translational movement along the axis of the rod; thus a permanent sliding contact between the bearing body and the tibial bearing surface is guaranteed, regardless of the angular position of the steering rod.

The steering rod preferably comprises a body-compatible metal alloy (titanium alloy), as does the tibial part.

In the following, embodiments of a knee-joint endoprosthesis in accordance with the invention are described in greater detail with reference to the attached drawings, wherein

BRIEF DESCRIPTION OF THE DRAWINGS

FIG. 1 shows a first embodiment of a knee-joint endoprosthesis (tibial part) in accordance with the invention, in posterior-anterior longitudinal section;

FIG. 2 shows the knee-joint endoprosthesis according to FIG. 1 in medial-lateral longitudinal section;

FIG. 3 shows the knee-joint endoprosthesis according to FIGS. 1 and 2 in plan view;

FIG. 4a shows part of a second embodiment of a knee-joint endoprosthesis in anterior-posterior longitudinal section;

FIG. 4b shows a section throuh the steering rod according to FIG. 4a;

FIG. 5 shows the knee-joint endoprosthesis according to FIG. 4a in medial-lateral longitudinal section;

FIG. 6 shows a third embodiment of a knee-joint endoprosthesis in accordance with the invention in medial-lateral longitudinal section;

FIG. 7 shows the knee-joint endoprosthesis according to FIG. 6 in posterior-anterior longitudinal section (along the line A—A in FIG. 8);

FIG. 8 shows the knee-joint endoprosthesis according to FIGS. 6 and 7 in plan view;

FIG. 9 shows part of a knee-joint endoprosthesis in accordance with the invention in medial-lateral longitudinal section so as to make clear a detail concerning the fixation of the bearing body on the tibial part;

DESCRIPTION OF THE PREFERRED EMBODIMENTS

Figure 4B:

As shown in FIGS. 1 to 3, a first embodiment of a knee-joint endoprosthesis comprises a tibial part 20 with a tibial bearing surface 7 on which a bearing body 1 is disposed so that it can move in the anterior-posterior direction (double-headed arrow 21 in FIG. 3). The bearing body comprises two bearing shells 8 with a concave curvature, so that a femoral joint part (femoral sled, not shown) can be movably seated therein.

In addition, a rotational guide means is provided for the bearing body 1, which guides the bearing body 1 over the tibial bearing surface 7 as it rotates about an axis 22 perpendicular to that surface (see double-headed arrow 29 in FIG. 3). The rotational guide means comprises a steering rod 23, which at one end is seated in the bearing body 1 so as to be both rotatable and pivotable with respect to the bearing body, and at the other end is guided medially and laterally within the tibial part 20, or in a housing 3 of the tibial part that extends further distally, within a slot-like recess 24 that extends in the anterior-posterior direction. The steering rod 23 in this embodiment is designed as a round bolt. At its proximal end the steering rod 23 bears a spherical head 2, which engages a pivot-bearing recess in the bearing body 1 that has a complementary shape, and in particular can be locked therein against movement from proximal to distal.

The slot-like recess 24 is a pocket hole that expands like a wedge from distal to proximal (See FIG. 1). Medially and laterally it is delimited by walls 25, 26 that extend parallel to one another and approximately perpendicular to the tibial bearing surface 7; the distance of these walls from one another is slightly greater than the diameter of the steering rod 23 or section thereof that is inserted into the pocket hole 10. The steering rod 23 is thus seated in a sliding bearing with clearance between the limiting walls 25, 26.

Because of the above-mentioned trapezoidal or wedge-like expansion of the pocket hole, it is possible for the steering rod 23 to make a tilting movement within the recess 24 in the anterior-posterior direction, as shown by the double-headed arrow 27 in FIG. 1. Accordingly, the bearing body can also be shifted in the posterior-anterior direction on and parallel to the tibial bearing surface 7.

The sliding bearing of the steering rod 23 in the tibial part 20 is brought about within a bearing sleeve 4 made of plastic, in particular polyethylene, such that this bearing sleeve 4 is positioned in the tibial part 20 so as to be secured against rotation; that it, is within the distally extending tibial housing 3.

As late as the closing phase of the operation the surgeon can still decide whether to insert a bearing sleeve 4 that permits only a rotational movement of the bearing body 1, or whether it should provide for both a rotational movement and a translational movement in the posterior-anterior direction. The surgeon can also choose from a set of bearing sleeves with recesses 24 that differ in length in the posterior-anterior direction, with the consequence that the abutment that stops the translational movement in the anterior direction or in the posterior direction is correspondingly differently positioned.

The limitation of the anterior-posterior translational movement is maintained by the anterior and posterior boundaries of the recess. These limit the tilting movement of the steering rod.

The embodiment according to FIGS. 4a to 5 is characterized in that at the proximal end of a steering rod 23' there is disposed a pivotal axle 6 that extends approximately parallel to the tibial bearing surface 7 in the medial-lateral direction, passing through a corresponding cross-bore in the steering rod 23'. As shown in FIG. 4b, the cross section of the steering rod 23' is flattened. This is an advantageous means of providing that the steering rod 23' contacts the medial and lateral limiting walls of the bearing sleeve (not shown) not along a line but rather over an area.

The pivotal axle 6 extends into a pivot-bearing recess 1a' of complementary shape in the bearing body 1'. This is a customary feature of such constructions, which need not be described further here.

The embodiment according to FIGS. 6 to 8 differs from that according to FIGS. 4a to 5 in that a modified steering rod 23" is pivotably seated by its distal end in the tibial part 20, such that this distal and/or the proximal pivot bearing at the bearing body 1' allows a translational movement along the axis of the rod, ensuring a permanent sliding contact between the bearing body 1' and the tibial bearing surface 7, regardless of the degree of tilt of the steering rod 23". This relative translational movement along the rod axis is indicated in FIG. 7 by the double-headed arrow 28.

The distal pivot bearing of the steering rod 23" is likewise defined by a pivotal axle 30 that extends through the steering rod 23" and a complementary receiving bore 4a' in the bearing housing 4', the pivotal axle 30 being oriented parallel to the pivotal axle 6 in the bearing body 1'.

In the embodiments according to FIGS. 4 to 8 the seating of the steering rod in the bearing body is only pivotabe. Therefore the bearing sleeve at the tibial part must be seated in such a way that it can be rotated about its long axis, in order to enable optimal guidance, suitable to the anatomy.

The embodiment according to FIG. 9 corresponds substantially to that according to FIGS. 1–3; only a (modified) bearing body 1" and a modified tibial housing 3' are shown here, in a medial-lateral longitudinal section. This embodiment is distinguished by the fact that the bearing body 1" interlocks on its medial and lateral sides with the tibial housing 3', so that it is ensured that the bearing body 1 will not be lifted away from the tibial bearing surface 7. The projections of the tibial housing 3 that extend into the bearing body 1 have posterior and anterior stopping devices (not shown) that limit the rotation of the bearing body 1. It is possible to space the lateral stopping devices further apart from one another than the medial ones, with the consequence that the bearing body 1" has greater freedom to move laterally than medially. This differential freedom of movement corresponds to the natural movement properties of a knee.

The above-mentioned rotation limiters for the bearing body on its medial and lateral sides can of course also be provided independently of the measures for locking the bearing body to the tibial housing on its medial and lateral sides; that is, they can be provided in all the embodiments described here.

Regarding the means for interlocking with the bearing body, it should also be mentioned that they act with sufficient play in the medial and lateral direction that the bearing body can move unhindered on the tibial bearing surface in the manner determined by the rotation-translation steering rod. The measures described above serve exclusively to keep the bearing body in sliding contact with the tibial bearing surface.

The bearing body is made of plastic as is usually the case, preferably polyethylene, whereas the tibial housing is made of a body-compatible metal alloy (titanium alloy), as is the steering rod including its pivot-bearing head or pivotal axis.

Figure 10A:
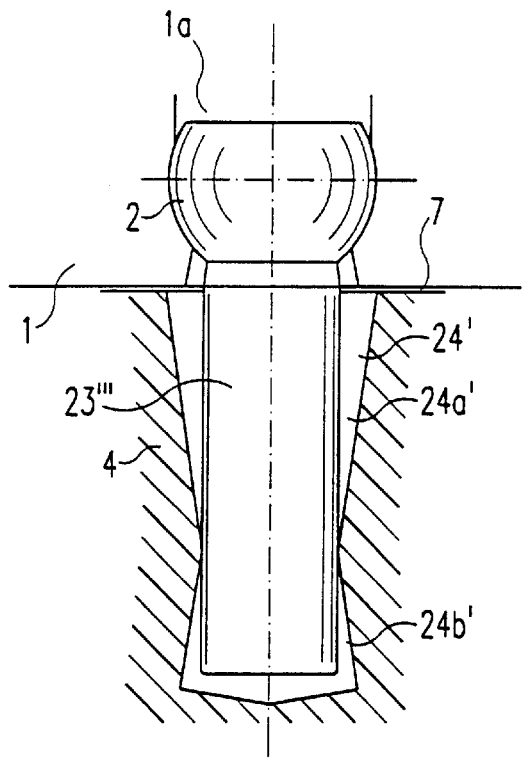
FIGS. 10a to 10c show part of another embodiment of the knee-joint endoprosthesis in accordance with the invention in anterior-posterior longitudinal section.
Figure 10B:
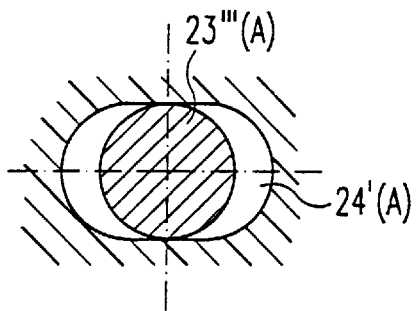
Figure 10C:
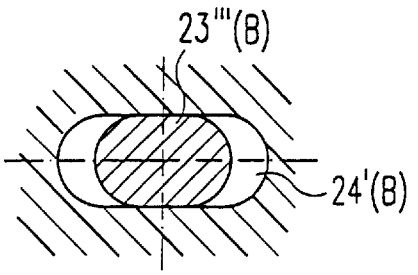

FIGS. 10a to 10c are diagrams of part of another embodiment, in which a steering rod 23'" with a cylindrical shaft section and pivot-bearing head 2 shaped like a segement of a sphere is held within the pivot-bearing recess 1a of a bearing body 1 constructed in accordance with FIGS. 1 to 3. The shaft section of the rod extends into a recess (a pocket hole) 24' comprising a first section 24a' that expands upward (towards the proximal opening) in the posterior-anterior direction so as to have a trapezoidal shape, and a second section 24b' that expands downward (towards the distal end), likewise having a substantially trapezoidal shape. This configuration of the recess 24' allows the steering rod 23'" to be pivoted freely in the posterior-anterior direction about a pivotal axis situated at the level of the narrowest part of the recess 24'.

In FIGS. 10b and 10c cross-sectional shapes of the shaft of the rod 23'" and the recess 24' (at the level of the tibial bearing surface 7) are sketched. To indicate how the two variants are related to FIG. 10a, here the parts are identified by the symbols 23'" (A) or 23'" (B) and 24' (A) or 24' (B).

Figure 11A:
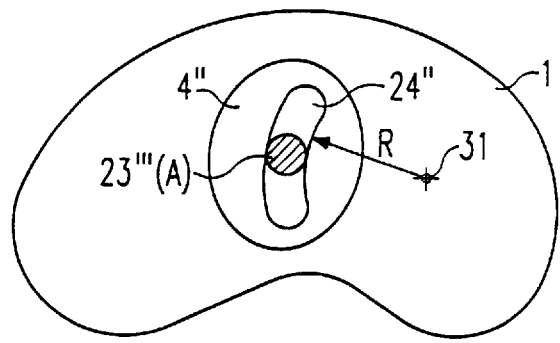
FIGS. 11a and 11b are a schematic representation of another embodiment of the knee-joint endoprosthesis in plan view and cross section, respectively.
Figure 11B:
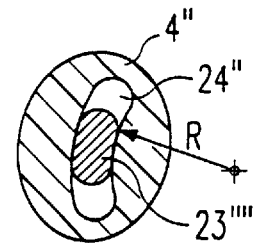

FIGS. 11a and 11b are sketches to show the principles of another embodiment, in which below the bearing body 1 there is provided a bearing sleeve 4" with a curved recess 24" in which is guided a steering rod 23'" (A) with circular shaft cross section (FIG. 11a) or a steering rod 23'"" with shaft cross section adapted to the curvature of the recess 24". The recess 24" is curved about a center of curvature 31 on the medial side with a radius of curvature R, in such a way that it is concave on the side facing medially, i.e. convex on the side facing laterally. In the embodiment according to FIG. 11b this also applies to the shaft cross section of the steering rod 23'"".

Figure 12:
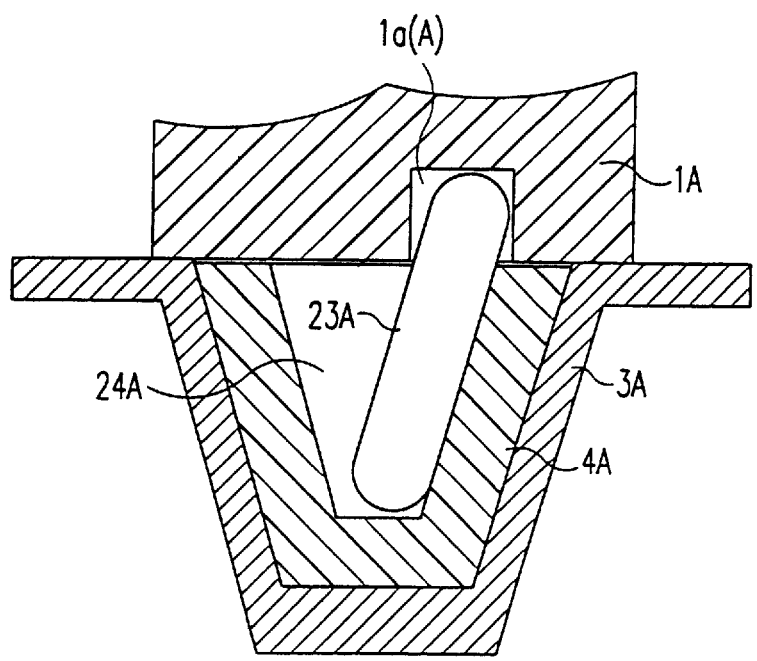
FIG. 12 illustrates in principle the general possibilities for constructing the knee-joint endoprosthesis in accordance with the invention (as posterior-anterior longitudinal section).

FIG. 12 is a simplified sketch to explain the most essential functional components and basic principles of operation of the proposed arrangement. It comprises a bearing body 1A in which is formed a pivot-bearing recess 1a (A), as well as a tibial housing 3A containing a bearing sleeve 4A in which is formed a recess 24A, and finally a steering rod 23A. The guide means diagrammed here would fundamentally be at risk of luxation, so that in this respect the drawing should be understood as greatly simplified. However, it shows the principle underlying the rotational guidance of the bearing body 1A by the steering rod 23A, which is seated so that it can pivot relative to the bearing body and be displaced in the medial-lateral direction.

All the characteristics disclosed in the application documents are claimed as essential to the invention insofar as they are new to the state of the art individually or in combination.

| List of reference numerals | |
|---|---|
| 1' 1'; 1"; 1A | Bearing body |
| 1a; 1a'; 1a(a) | Pivot-bearing recess |
| 2 | Pivot-bearing head |
| 3; 3'; 3A | Tibial housing |
| 4; 4'; 4"; 4A | Bearing sleeve |
| 4a' | Receiving bore |
| 6, 30 | Pivotal axle |
| 7 | Tibial bearing surface |
| 8 | Bearing shell |
| 20 | Tibial part |
| 21, 27, 28, 29 | Double-headed arrow |
| 22 | Axis of rotation |
| 23; 23'; 23"; 23'" 23'"(A); 23'"(B) 1 23A | Steering rod |
| 24; 24'; 24'(A); 24'B; 24"; 24A | Slot-like recess (pocket hole) |
| 24a', 24b' | Sections of recess |
| 25, 26 | Limiting wall |
| 31 | Center of curvature |
| R | Radius of curvature |

What is claimed is:

1. A knee-joint endoprosthesis with a tibial part having a flat tibial bearing surface, with a bearing body that can be shifted thereon in the anterior-posterior direction and comprises two concave bearing shells within which a femoral joint part can be movably seated, and with a rotational guide that permits rotation of the bearing body on the tibial bearing surface about an axis of rotation perpendicular to the tibial bearing surface, and wherein the rotation guide comprises a steering rod that is seated at the bearing body so as to be pivotable relative thereto and at the tibial part is guided in at least one of the medial/lateral direction and rotationally; wherein the steering rod is pivotable about an axis that is substantially parallel to the flat tibial bearing surface.

2. The knee-joint endoprosthesis of claim 1, wherein the steering rod is guided at the tibial part medially and laterally within a slot-like recess and is either held at the bearing body so as to be rotatable and pivotable relative thereto or is only pivotably held at the bearing body and together with the recess in the tibial part is seated so as to be rotatable about an axis of rotation perpendicular to the tibial bearing surface.

3. The knee-joint endoprosthesis of claim 2, wherein the slot-like recess is constructed as a pocket hole, which, towards the tibial bearing surface expands in a trapezoidal shape from distal to proximal, at least in its upper region, and medially and laterally is bounded by two walls that extend parallel to one another and approximately perpendicular to the tibial bearing surface and, to allow a clearance fit, are spaced apart from one another by a distance slightly greater than the corresponding dimension of the steering rod or section thereof that is contained within the recess.

4. The knee joint endoprosthesis of claim 3, wherein the pocket hole in its lower region expands in the anterior-posterior direction away from the tibial bearing surface in a trapezoidal shape, so as to ensure that the steering rod can pivot about a pivotable axis spaced apart from its distal end substantially without bending.

5. The knee-joint endoprosthesis of claim 2, wherein the slot-like recess exhibits a curvature determined by a radius of curvature about a center of curvature situated medially with respect to the recess, so that the recess has a concave shape on the side facing medially and a convex shape on the side facing laterally.

6. The knee-joint endoprosthesis of claim 5, wherein the curvature is in the shape of a circular arc.

7. The knee-joint endoprosthesis according to claim 5 wherein at least the section of the steering rod contained within the slot-like recess is substantially cylindrical or shaped like a truncated cone, or has two curved wall sections that are cylindrical or shaped like a truncated cone, so as to adapt the steering rod to the curvature of the recess.

8. The knee-joint endoprosthesis of claim 2, wherein the steering rod or at least the section thereof contained within the slot-like recess comprises at least two wall sections shaped like segments of a cylinder or of a truncated cone.

9. The knee-joint endoprosthesis according to claim 8 herein at least the section of the steering rod contained within the slot-like recess is substantially cylindrical or shaped like a truncated cone, or has two curved wall sections that are cylindrical or shaped like a truncated cone, so as to adapt the steering rod to the curvature of the recess.

10. The knee-joint endoprosthesis according to claim 8, wherein at least the section of the steering rod contained within the slot-like recess, in the case in which the recess has flat wall sections, comprises two flat wall sections that connect the sections of the steering rod that are shaped like a cylinder or truncated cone.

11. The knee-joint endoprosthesis of claim 1, wherein the steering rod at its proximal end comprises a spherical head or a pivotable axle extending in the medial-lateral direction substantially parallel to the tibial bearing surface, such that either head or axle inserts into a pivot-bearing recess at the bearing body that has a complementary shape.

12. The knee-joint endoprosthesis of claim 1 further comprising a bearing sleeve and wherein the guidance of the steering rod at the tibial part is brought about within the bearing sleeve and wherein the bearing part is made of plastic and is positioned at the tibial part so as to be secured against rotation.

13. The knee-joint endoprosthesis of claim 12, wherein the bearing sleeve is seated within a tibial housing comprising a pocket hole that expands towards the tibial bearing surface, into which the bearing sleeve is inserted.

14. The knee joint endoprosthesis of claim 6, wherein the plastic comprises polyethylene.

15. The knee-joint endoprosthesis of claim 1 wherein the steering rod is pivotably mounted by way of its distal end at the tibial part, such that at least one of this distal pivot bearing and the proximal pivot bearing at the bearing body permits a translational movement along the axis of the rod, so that a permanent sliding contact between the bearing body and the tibial bearing surface is ensured regardless of the pivotal position of the steering rod.

16. The knee-joint endoprosthesis of claim 1, wherein at least one of the ends of the steering rod contained within the bearing body and the end guided at the tibial part is rounded to form substantially a section of a sphere.

17. A knee-joint endoprosthesis with a tibial part having a flat tibial bearing surface, with a bearing body that can be shifted thereon in the anterior-posterior direction and comprises two concave bearing shells within which a femoral joint part can be movably seated, and with a rotational guide that permits rotation of the bearing body on the tibial bearing surface about an axis of rotation perpendicular to the tibial bearing surface, wherein the rotation guide comprises a steering rod that is seated at the bearing body so as to be pivotable relative thereto and at the tibial part is guided in at least one of the medial/lateral direction and rotationally; wherein the steering rod at its proximal end comprises a spherical head or a pivotable axle extending in the medial-lateral direction substantially parallel to the tibial bearing surface, such that either head or axle inserts into a pivot-bearing recess at the bearing body that has a complementary shape.

18. The knee-joint endoprosthesis of claim 17, wherein the steering rod is guided at the tibial part medially and laterally within a slot-like recess and is either held at the bearing body so as to be rotatable and pivotable relative thereto or is only pivotably held at the bearing body and together with the recess in the tibial part is seated so as to be rotatable about an axis of rotation perpendicular to the tibial bearing surface.

19. The knee-joint endoprosthesis of claim 18, wherein the slot-like recess is constructed as a pocket hole, which, towards the tibial bearing surface expands in a trapezoidal shape from distal to proximal, at least in its upper region, and medially and laterally is bounded by two walls that extend parallel to one another and approximately perpendicular to the tibial bearing surface and, to allow a clearance fit, are spaced apart from one another by a distance slightly greater than the corresponding dimension of the steering rod or section thereof that is contained within the recess.

20. The knee-joint endoprosthesis of claim 18, wherein the steering rod or at least the section thereof contained within the slot-like recess comprises at least two wall sections shaped like segments of a cylinder or of a truncated cone.

21. The knee-joint endoprosthesis according to claim 20 wherein at least the section of the steering rod contained within the slot-like recess is substantially cylindrical or shaped like a truncated cone, or has two curved wall sections that are cylindrical or shaped like a truncated cone to adapt the steering rod to the curvature of the recess.

22. The knee-joint endoprosthesis according to claim 20, wherein at least the section of the steering rod contained within the slot-like recess, in the case in which the recess has flat wall sections, comprises two flat wall sections that connect the sections of the steering rod that are shaped like a cylinder or truncated cone.

23. The knee-joint endoprosthesis of claim 17 further comprising a bearing sleeve and wherein the guidance of the steering rod at the tibial part is brought about within the bearing sleeve and wherein the bearing part is made of plastic and is positioned at the tibial part so as to be secured against rotation.

24. The knee-joint endoprosthesis of claim 23, wherein the bearing sleeve is made of polyethylene.

25. The knee-joint endoprosthesis of claim 23, wherein the bearing sleeve is seated within a tibial housing comprising a pocket hole that expands towards the tibial bearing surface, into which the bearing sleeve is inserted.

26. The knee-joint endoprosthesis of claim 17, further comprising a plurality of bearing sleeves configured to guide the steering rod in one or both of a rotational motion, or a pivotal motion, wherein each of said sleeves is configured to restrict the steering rod to a different degree of motion.

27. The knee-joint endoprosthesis of claim 17, wherein the steering rod is pivotably mounted by way of its distal end at the tibial part, such that at least one of this distal pivot bearing and the proximal pivot bearing at the bearing body permits a translational movement along the axis of the rod, so that a permanent sliding contact between the bearing body and the tibial bearing surface is ensured regardless of the pivotal position of the steering rod.

28. The knee-joint endoprosthesis of claim 17, wherein the bearing body is made of polyethylene.

29. A knee-joint endoprosthesis with a tibial part having a flat tibial bearing surface, with a bearing body that can be shifted thereon in the anterior-posterior direction and comprises two concave bearing shells within which a femoral joint part can be movably seated, and with a rotational guide that permits rotation of the bearing body on the tibial bearing surface about an axis of rotation perpendicular to the tibial bearing surface, wherein the rotation guide comprises a steering rod that is seated at the bearing body so as to be pivotable relative thereto and at the tibial part is guided in at least one of the medial/lateral direction and rotationally; wherein at least one of the ends of the steering rod contained within the bearing body and the end guided at the tibial part is rounded to form substantially a section of a sphere.

30. The knee-joint endoprosthesis of claim 29, wherein the steering rod is guided at the tibial part medially and laterally within a slot-like recess and is either held at the bearing body so as to be rotatable and pivotable relative thereto or is only pivotably held at the bearing body and together with the recess in the tibial part is seated so as to be rotatable about an axis of rotation perpendicular to the tibial bearing surface.

31. The knee-joint endoprosthesis of claim 30, wherein the slot-like recess is constructed as a pocket hole, which, towards the tibial bearing surface expands in a trapezoidal shape from distal to proximal, at least in its upper region, and medially and laterally is bounded by two walls that extend parallel to one another and approximately perpendicular to the tibial bearing surface and, to allow a clearance fit, are spaced apart from one another by a distance slightly greater than the corresponding dimension of the steering rod or section thereof that is contained within the recess.

32. The knee-joint endoprosthesis of claim 30, wherein the steering rod or at least the section thereof contained within the slot-like recess comprises at least two wall sections shaped like segments of a cylinder or of a truncated cone.

33. The knee-joint endoprosthesis according to claim 32 wherein at least the section of the steering rod contained within the slot-like recess is substantially cylindrical or shaped like a truncated cone, or has two curved wall sections that are cylindrical or shaped like a truncated cone to adapt the steering rod to the curvature of the recess.

34. The knee-joint endoprosthesis according to claim 32, wherein at least the section of the steering rod contained within the slot-like recess, in the case in which the recess has flat wall sections, comprises two flat wall sections that connect the sections of the steering rod that are shaped like a cylinder or truncated cone.

35. The knee-joint endoprosthesis of claim 29 further comprising a bearing sleeve and wherein the guidance of the steering rod at the tibial part is brought about within the bearing sleeve and wherein the bearing part is made of plastic and is positioned at the tibial part so as to be secured against rotation.

36. The knee-joint endoprosthesis of claim 35, wherein the bearing sleeve is made of polyethylene.

37. The knee-joint endoprosthesis of claim 35, wherein the bearing sleeve is seated within a tibial housing comprising a pocket hole that expands towards the tibial bearing surface, into which the bearing sleeve is inserted.

38. The knee-joint endoprosthesis of claim 29, further comprising a plurality of bearing sleeves configured to guide the steering rod in one or both of a rotational motion, or a pivotal motion, wherein each of said sleeves is configured to restrict the steering rod to a different degree of motion.

39. The knee-joint endoprosthesis of claim 29, wherein the bearing body is made of polyethylene.

* * * * *